United States Patent [19]

Herve et al.

[11] Patent Number: 4,897,266

[45] Date of Patent: * Jan. 30, 1990

[54] NOVEL PHYSIOLOGICAL PRODUCT EXTRACTED FROM ALGAE AND PLANTS

[75] Inventors: Rene A. Herve, Plancoët; Serge Percehais, Saint Malo, both of France

[73] Assignee: Laboratoires Goemar S.A., France

[*] Notice: The portion of the term of this patent subsequent to Apr. 8, 2003 has been disclaimed.

[21] Appl. No.: 185,241

[22] Filed: Apr. 18, 1988

Related U.S. Application Data

[63] Continuation of Ser. No. 884,673, Jul. 16, 1986, abandoned, which is a continuation of Ser. No. 638,463, filed as PCT FP83/00267 on Dec. 29, 1983, abandoned.

[30] Foreign Application Priority Data

Dec. 30, 1982 [FR] France .............................. 82 22136
Dec. 30, 1982 [FR] France .............................. 82 22137
Nov. 30, 1983 [FR] France .............................. 83 19142

[51] Int. Cl.[4] .............................................. A61K 35/78
[52] U.S. Cl. .................................. 424/195.1; 426/590; 426/652; 426/653
[58] Field of Search ...................... 424/195.1; 426/590, 426/684

[56] References Cited

U.S. PATENT DOCUMENTS 4,023,734  5/1977  Hervë et al. .......................... 241/23
4,581,233  4/1986  Herv',uml/e/ et al. ......... 424/195.1

FOREIGN PATENT DOCUMENTS 2022459  12/1979  United Kingdom .................. 241/30

Primary Examiner—John W. Rollins
Attorney, Agent, or Firm—Bacon & Thomas

[57] ABSTRACT

The present invention relates to a new physiological product extracted from algae and plants (e.g. artichokes), the process and apparatus used in its preparation by a combination of cryocomminution and molecular milling followed by ultra-decantation and ultra-filtration to obtain a sterile microburst product are described.

18 Claims, 5 Drawing Sheets

NOVEL PHYSIOLOGICAL PRODUCT EXTRACTED FROM ALGAE AND PLANTS

This application is a continuation, of application Ser. No. 884,673, filed July 16, 1986, now abandoned, which is a continuation of Ser. No. 638,463, filed as PCT FR83/00267 on Dec. 29, 1983, now abandoned.

The present invention relates to a complex process for treating diverse algae and plants which combines several precise steps of treatment, thanks to which an original product of extraction has been obtained, hereinafter called "physiological filtrate".

It is known to treat algae and plants by "cryocomminution" from French Patent No. 74 35162 filed on 18th Oct. 1974 by HERVE and ROUILLER.

According to this Patent, the algae and plants are cut then frozen to $-20°/-50°$ C., then are ground at that temperature in a mill incorporating cutters and teeth disposed in series. A detailed description of the equipment is given in said Patent. The algae and plants (average dimension 0.1–0.5 mm) are then sent towards one or more additional mills, at ambient temperature, for example mills incorporating three cylinders (a dimension of 100 to 50$\mu$ or even 10$\mu$ is thus attained). The features of these apparatus are also described in said Patent.

A thick green pulp is thus obtained, with a pH close to 4.8, which, thanks to the cryocomminution, contains almost all the useful and beneficial substances contained in the starting algae and plants (cf. Table I of the Patent mentioned above).

It has been discovered, according to the invention, that the combination of four operations:
(1) cryocomminution as defined hereinabove,
(2) molecular milling using specific equipment
(3) turbodecantation (decantation at high speed)
(4) selective ultrafiltration
make it possible to obtain a novel extract of algae and plants presenting certain properties.

One of the essential elements of the invention resides in the combination of the two milling operations (1) and (2).

In particular, this "physiological filtrate" is bereft of cellular matter, cellulose, components with long molecular chain, and is directly assimilable (it contains microelements, vitamins, micropeptides).

One of its essential features is that it does not contain residual alcohols coming from the extraction steps.

It can be used in balanced booster oligotherapy and to promote, by synergistic effect, the assimilation of oligo-elements and vitamins, at a rate of 10 to 50 ml of pure product per day and per adult.

The process which enables this original extract to be obtained will be described hereinafter.

The fresh algae or plants are cut then undergo a cryocomminution as described hereinabove.

Figure 1:
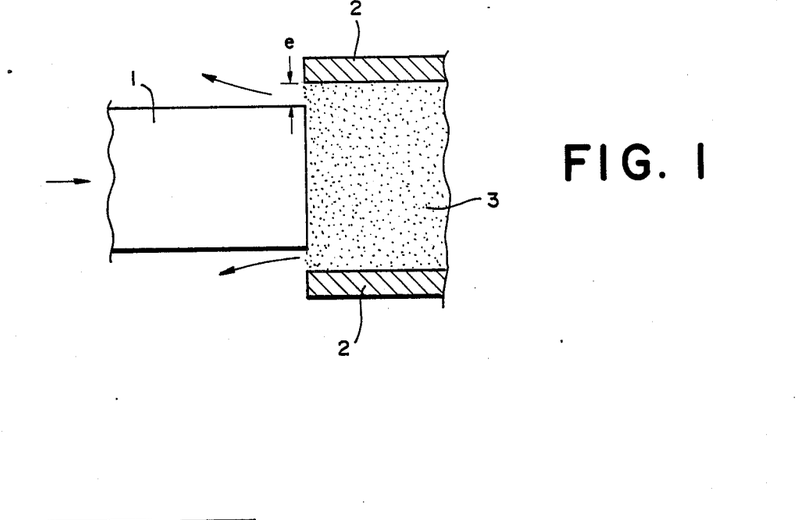

The pulp obtained is then sent into a specific molecular mill as shown in accompanying FIG. 1.

The specific mill necessary for obtaining the product according to the invention consists in a piston 1/valve 2 assembly comprising between the piston and the valve an extremely small space e (of the order of 0.035 mm under 350 bars and at 400 liters/hr.).

The principle is known: the piston, by its reciprocating movement, drives the product 3 to be treated through the space e where the product is milled.

This process makes it possible to obtain a product milled in a novel manner, which releases principles other than those released by the known processes, and in a different manner.

This may perhaps be explained by the synergistic effect which is observed, at milling level, between the two types of mills.

Molecular milling considerably modifies the product, since it passes its flow time from for example 24 to 59 s (much more viscous product).

It is also essential to emphasize that, for the first time, a sterile product leaves the mills, which is of decisive importance in the applications envisaged.

The process of bursting based on a sudden drop in pressure, which may become negative (cavitation effect), apart from the bursting of the vegetative cells, brings about bursting of the micro-organisms and in particular of the bacteria. A sterile product may thus be obtained provided, however, that the initial bacterial pollution is not too high.

The combination of the two mills therefore makes it possible to obtain:

a more active product due to the greater percentage of burst cells releasing a larger quantity of intracellular liquid;

a better conservation of the active ingredients, particularly of the enzymatic properties conserved thanks to a low temperature being maintained during the whole chain of operations;

products presenting a good resistance in time thanks to the sterilization obtained at the moment of milling (bursting during compression-decompression); this quality is particularly important in the case of cosmetic applications.

Moreover, the combination with the cryocomminution technique allows whole algae or plants to be treated, for the first time.

The combination of steps according to the invention therefore does not make an extraction but a "reduction" of the whole plant in a micro-burst form.

Finally, the presence of the "molecular" or "cellular" mill in the chain makes it possible to carry out an ultrafiltration which is impossible to effect without this mill. Between the cellular grinding and ultra-filtration, an ultra-decantation is effected, which is also indispensable.

The process according to the invention consequently consists in the combination of the following steps:
cryocomminution
passage in the molecular mill
ultra-decantation
ultra-filtration.

For certain well-determined products, it may be envisaged to dispense with the molecular mill, but not in the general case.

Step (3) consists in a turbo-decantation with pipetting of the product at the centre of the bowl.

Step (4) of ultra-filtration is effected on charcoal filters comprising a layer of zirconium oxide, membrane M4 [having a power of cut of less than 20.000 (separating the molecular weights >20.000)]. This step of ultrafiltration contributes to acquiring the sterile character.

After step (4), the product is packed in a sterile room (or "clean room") to preserve the sterility of the product which is one of the essential results of the invention.

Figure 2:
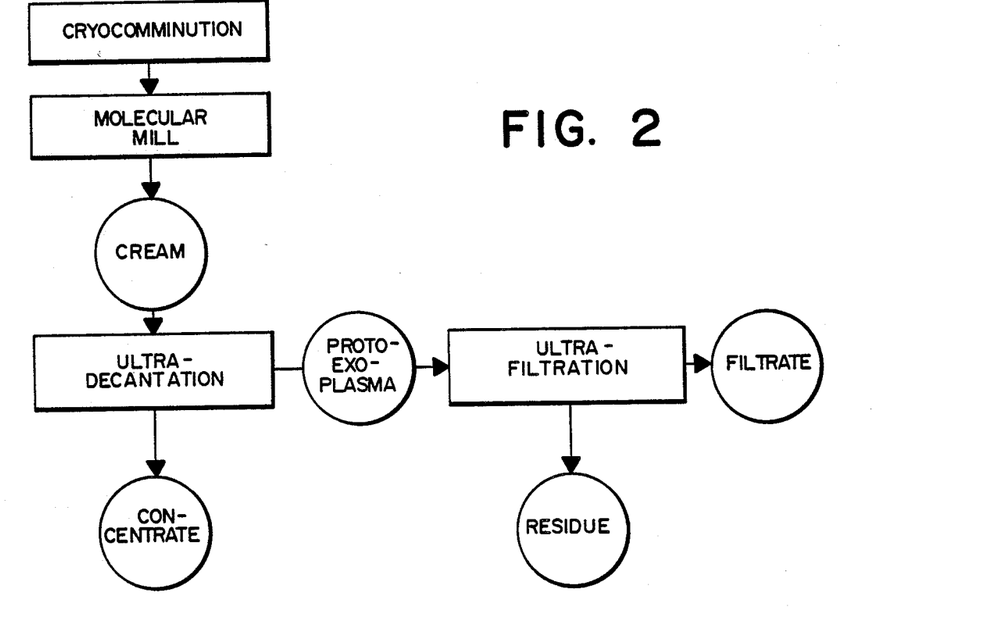

The chain of operations as well as the products obtained are shown in accompanying FIG. 2.

In the case of algae, the "concentrate of centrifugation" contains mainly cellular debris and alginates. It may be used for activating composts and for treating certain effluents.

The "residue" comprises molecules of molecular weight greater than 20.000, in particular polysaccharides.

It may be used for producing products for external use, using to advantage the heparin-like properties of the sulfuryl polysaccharides.

The filtrate contains virtually all the oligo-elements, 80% of the polysaccharides, the phytohormones and vitamins, and, in general, all the molecules of weight less than 20.000.

It may be used for manufacturing homeopathic mother tincture, cosmetic products, phytotherapeutic products and drinks.

The following Examples illustrate the invention without, however, limiting the scope thereof.

EXAMPLE 1

Filtrate of algae (Laminaria)

The physiological filtrate "GYFL" is a protocellular liquid of selected fresh algae (particularly Laminaria), highly purified by a physical cold process (cryocomminution, molecular milling, turbo-decantation and selective ultra-filtration).

Cryocomminution and molecular milling:

The fresh algae are milled cold ($-40°$ C.), this enabling a cream of algae to be obtained, whose fineness is less than $20\mu$.

Turbodecantation

The cream of algae is decanted at high speed, enabling the cellulose and the insoluble alginates to be eliminated.

Selective ultra-filtration:

An ultra-fine filtration enables a liquid without impurities to be obtained, whose coompponents have a molecular weight of less than 20.000.

PROPERTIES:

Exempt of cellular matter, cellulose, components with long molecular chain, the physiological filtrate of algae GYFL is directly assimilable (microelements, vitamins, micropeptides).

Assimilation is promoted by a modified distribution of molecular weight: % of molecules of low MW is greater than the % of molecules of high MW.

The process of manufacture enables a product of high bacteriological quality to be obtained.

Without conserving agent, without dye-stuff, without alcohol.

USE IN DIETETICS balanced booster oligotherapy

Vector for assimilation of oligo-elements and vitamins

To be used diluted at the dose of 10 to 50 ml of pure product per day.

The results of analyses carried out on this product will be found hereinbelow.

DRY MATTER-PROTEINS-LIPIDES-GLUCIDES-ASH

Methods used for dosing the proteins, glucides, lipides and ash of the filtrate "GYFL".

(1) Dosage of the proteins:

The protein content is assessed from the total amount of nitrogen multiplied by 6.25.

(2) Dosage of the lipides

The technique used is the one described by BLIGH and DYER (1959).

To the weighed sample (containing 80 g of water), 300 ml of a chloroform /methanol (1-2) solution are added with stirring. Stirring is maintained for 10 mins.

The insoluble residue is eliminated by filtration on WHATMAN 1 PS paper.

100 ml of chloroform and 100 ml of methanol are successively added to the limpid solution thus obtained.

The mixture is stirred after each addition.

The biphase mixture obtained is transferred to a separating funnel and left to stand for one night.

The heavy chloroform phase is collected then evaporated to dryness.

The lipid residue is taken up in a small quantity of methylene chloride.

This solution is evaporated in a calibrated, weighed tube.

E. G. BLIGH and W. J. DYER (1959) A rapid method of Total Lipid Extraction and Purification Canada I. of Biochem and Physial 37 (8), 911.

(3) Dosage of the glucides

The method used is that of DUBOIS et coll. (1956).

The modus operandi used is described hereinafter. The results are expressed in glucose equivalent.

"Dosage of the sugars by the DUBOIS method"

Object and domain of application

This is a colorimetric method which is simple, rapid and sensitive, applicable to the reducing sugars (hexoses, pentoses, disaccharides, polysaccharides), to their methyl derivatives and to uronic acids. It should be indicated that the glucosamines and galactosamines are not taken into account.

Reagents

PHENOL rectapur, PROLABO (prepare a 5% solution)

Sulfuric acid NORMAPUR PROLABO (98.08%, d=1.83)

Standard solution of glucose or galactose at 10 mg for 50 ml)

Equipment a visible spectrophotometer (tungsten lamp) (OS glass vats). Analysis was carried out on a BECKMANN ACTA III apparatus.

a VORTEX a series of tubes of 15 or 20 ml a series of micropipettes of the EPPENDORF type Modus operandi calibration curve: take between 20 and 200 $\mu$g of standard which is adjusted to 2 ml of $H_2O$. Do not forget to provide a blank.

Add 1 ml of 5% phenol

Stir well in vortex

Add 5 ml of concentrated $H_2SO_4$, stir and allow coloration to develop.

Read the absorption at 485 nm after 30 minutes

M. DUBOIS, K. A. GILLES, J. K. HAMILTON, P. A. REBERS and F. SMITH (1956)- "Colorimetric method for determination of sugars and related substances". Analytical Chemistry 28 (3), 350.

(4) Dosage of the ash

The quantity of inorganic matter is assessed by the amount of ash remaining after combustion.

10 to 20 g of sample are spread on the bottom of a calibrated Petri dish.

The sample is firstly oven-dried at 80° C. then transferred to an oven.

The temperature rises from 20° C. to 550° C. in 24 hours and this temperature is maintained for 48 hours.

The product is weighed after complete cooling in a desiccator.

Due to the small quantity of raw material available, the dosage of the lipides of GYFL was effected on 1 ml. Consequently, the given value is approximate. A first measurement gave 0.03%, a second 0.04%.

The results are shown in Tables I to III hereinbelow.

The index of primary irritation of a physiological filtrate GYFL was also determined by the method described in the Journal Officiel of 21st Feb. 1982.

The test was made on six male Albino rabbits, of defined strain, weighing about 2.5 kg, having dwelt for a minimum of one week in individual cages in the animal house in order to be perfectly acclimatized. During the test, the rabbits were held in restraining boxes. The day before the application of the product to be tested, they were shorn on their backs and sides with an electric clipping machine provided with a comb with a height of cut of 0.05 mm in order to clear a surface of about 14×14 cm. Before beginning the test, we made sure that the animals' skins were healthy and hairless.

On day zero, with the aid of a sterile vaccinostyle, we made three parallel scarifications over a length of about 2.5 cm spaced apart by about 0.5 cm, on the right-hand side of each rabbit, without reaching the dermis, i.e. without causing bleeding.

0.5 ml of physiological filtrate GYFL are deposited with the aid of a sterile syringe of 1 ml of within a tenth, on two pieces of 8 thicknesses of Codex absorbent gauze, with a surface of 6.2 cm², of which one of the surfaces is covered with an impermeable hypoallergenic adhesive film, said pieces applied immediately on the skin, maintained in contact with the skin on each of the two zones by a hypoallergenic microporous adhesive tape of 50 mm width. A protective compress made of Codex absorbent gauze of appropriate dimensions is then placed thereon; the whole is held in place by a bandage.

Twenty four hours after the application of the product, the cutaneous primary irritation is assessed. It is assessed 30 minutes after the removal of the dressing and again forty eight hours later, i.e. seventy two hours after the application of the product.

The observations are made on the two zones, scarified and non-scarified, in accordance with the following numerical scale:

| Erythema and formation of eschars | |
|---|---|
| No erythema | 0 |
| Slight erythema | 1 |
| Clearly visible erythema | 2 |
| Considerable erythema | 3 |
| Serious erythema (purple-red, deep lesions) | 4 |
| Formation of oedemas | |
| No oedema | 0 |
| Very slight oedema | 1 |
| Slight oedema (well defined contours, apparent swelling) | 2 |
| Average oedema (thickness about 1 mm) | 3 |
| Serious oedema (thickness greater than 1 mm and surface larger than that of the zone of application) | 4 |

The figures obtained for the erythema and for the oedema are added after twenty four hours and seventy two hours, on the one hand on the six non-scarified zones, on the other hand on the six scarified zones.

The figures thus obtained are added and the average is calculated by dividing the total by 24.

This average represents the index of cutaneous primary irritation (P.I.).

The results are expressed as follows:
NON-IRRITANT P.I.≦0.5
SLIGHTLY IRRITANT 0.5<P.I.≦2
IRRITANT 2<P.I.≦5
VERY IRRITANT 5<P.I.≦8

The results obtained for each rabbit are shown in Table IV hereinafter.

The index thus determined is equal to 0.04, which corresponds to a product considered legally, according to the Decree of 1st Feb. 1982 which appeared in the Journal Officiel of 21st Feb. 1982, as nonirritant.

SHORT TERM TOXICITY-DETERMINATION OF THE LD 50

Assessment of the LD 50 consists in determining the lethal dose for 50% of the animals experimented on: male and female rats of Wistar strain.

This determination supposes certain conditions, namely:
the volume used must, at maximum, be 0.5 ml per 20 g of body weight;
the concentration of active ingredient must be known as well as the nature of the excipient.

Taking into account the texture and the composition of the cream of algae GYFL, the active ingredient cannot be identified as such and we therefore tested the cream of algae whole without adding excipient and chose the oral route by gastric cramming, as the route of administration.

The doses chosen ranged from 0.5 g to 2.5 g for 100 g of body weight.

At the dose of 2.5 g for 100 g of body weight, the deaths observed were in fact due to poor manipulation by the operator (asphyxia by pulmonary congestion).

It is therefore deduced that the LD 50 of the cream of algae GYFL is higher than 25 g/kg (limiting factor: no possibility of volumetric absorption).

TABLE I

RESULTS OF ANALYSES
The results are expressed in percentage of wet product

| Samples | Ash | Organic substances | | |
|---|---|---|---|---|
| | | Proteins | Lipides | Glucides* |
| GYFL | 0.312% | 0.12% | 0.02% | 0.756% |

*expressed in "glucose equivalent"

TABLE II

| | GYFL | | |
|---|---|---|---|
| | Method | Mineralization | Precision % |
| SODIUM | Flame spectrometry (a) | 1 | ±5 |
| POTASSIUM | Flame spectrometry (a) | 1 | 4 |
| LITHIUM | Flame spectrometry | 1 | 4 |
| CALCIUM | Atomic absorption (flame) - AFNOR V18-108 | 1 | 4 |
| MAGNESIUM | Atomic absorption (flame) (b) | 1 | 4 |

TABLE II-continued

| | | GYFL | |
|---|---|---|---|
| | Method | Mineralization | Precision % |
| STRONTIUM | Flame spectrometry | 1 | 4 |
| CHROMIUM | Colorimetry (Diphenyl Carbazide) | 2 | / |
| IRON | Atomic absorption (flame) (c) | 2 | ±5 |
| MANGANESE | Atomic absorption (flame) (c) | 2 | 4 |
| COPPER | Atomic absorption (oven) (c) | 2 | ±10 |
| COBALT | Atomic absorption (oven) | 2 | / |
| NICKEL | Atomic absorption (oven) | 2 | ±10 |
| ZINC | Atomic absorption (flame) (c) | 2 | ±5 |
| TIN | Atomic absorption (oven) | 2 | ±10 |
| LEAD | Atomic absorption (oven) | 2 | " |
| CADMIUM | Atomic absorption (oven) | 2 | " |
| MOLYBDENUM | Colorimetry (thiocyanate) | 2 | ±5 |
| ANTIMONY | Colorimetry (Rhodamine) | 2 | / |
| TITANIUM | Colorimetry (chromotropic acid) | 2 | ±10 |
| CHLORINE | Volumetry with silver nitrate (a) | 3 | ±3 |
| PHOSPHORUS | Colorimetry with heptamolybdate | 4 | ±5 |
| NITROGEN | Kjeldalh (volumetry) | 4 | ±5 |
| ARSENIC | Colorimetry (cf. AFNOR T 90201) | 2 | ±10 |
| BORON | Colorimetry (Curcumin) AFNOR T 90201 | 3 | ±3 |
| IODINE | Colorimetry (ceric salts method) | 3 | ±3 |
| BROMINE | Colorimetry (phenolsulfonephthaleine) | 3 | ±5 |
| SULFUR | Nepholometry (in SO4 form) | 1 | ±5 |
| FLUORINE | Colorimetry (zirconium method) AFNOR T 9004 | 3 | ±5 |
| MERCURY | Atomic absorption (flame) AFNOR T 90113 | 5 | ±10 |
| SELENIUM | Polarography | 6 | ±10 |

Observations:
1: Calcination and taking up of the ash in HCl
2: Wet mineralization $H_2SO_4 + HNO_3 + HClO_4$
3: Calcination in alkaline medium - take up of ash in water
4: Wet mineralization ($H_2SO_4 + H_2O_2$)
5: Wet mineralization ($H_2SO_4 + HNO_3 + KMNO$)
6: Attack by hydrobromic acid
Legend
(a) 1st C.E.E. directive (animal feed)
(b) 4th C.E.E. directive
(c) 8th C.E.E. directive
(d) 3rd C.E.E. directive

TABLE III

RESULTS OF ANALYSIS

| | GYFL |
|---|---|
| SODIUM (Na) mg/kg | 816 |
| POTASSIUM (K) mg/kg | 850 |
| LITHIUM (Li) µg/kg | ≦15 |
| CALCIUM (Ca) mg/kg | 150 |
| MAGNESIUM (Mg) mg/kg | 118 |
| STRONTIUM (Sr) mg/kg | 1.700 |
| CHROMIUM (Cr) mg/kg | <0.1 |
| IRON (Fe) mg/kg | 2.9 |
| MANGANESE (Mn) mg/kg | 0.34 |
| COPPER (Cu) mg/kg | 0.31 |
| COBALT (Co) µg/kg | <50 |
| NICKEL (Ni) µg/kg | 50 |
| MOLYBDENUM (Mo) µg/kg | <20 |
| ZINC (Zn) µg/kg | 2.0 |
| TIN (Sn) mg/kg | 17 |
| LEAD (Pb) mg/kg | <0.1 |
| CADMIUM (Cd) mg/kg | 0.042 |
| ANTIMONY (Sb) mg/kg | <0.01 |
| CHLORINE (Cl) mg/kg | 973 |
| PHOSPHORUS (P) mg/kg | 176 |
| NITROGEN (N) mg/kg | 188 |
| ARSENIC (As) mg/kg | 3.0 |
| BORON (B) mg/kg | 1.41 |
| IODINE (I) mg/kg | 1.8 |
| BROMINE (Br) mg/kg | 16 |
| SULFUR (S) mg/kg | 222 |
| TITANIUM (Ti) mg/kg | <1 |
| FLUORINE (F) mg/kg | 8.4 |
| MERCURY (Hg) mg/kg | <0.05 |
| SELENIUM (Se) mg/kg | |

TABLE IV

INDIVIDUAL RESULTS OF DETERMINATION OF THE INDEX OF PRIMARY IRRITATION OF PHYSIOLOGICAL FILTRATE GYFL

| | RESULTS AFTER 24 HOURS | | | | RESULTS AFTER 72 HOURS | | | |
|---|---|---|---|---|---|---|---|---|
| | SCARIFIED SIDE | | NON-SCARIFIED SIDE | | SCARIFIED SIDE | | NON-SCARIFIED SIDE | |
| RABBIT | Oedema | Erythema | Oedema | Erythema | Oedema | Erythema | Oedema | Erythema |
| 1 | 0 | 0 | 0 | 0 | 0 | 0 | 0 | 0 |
| 2 | " | 1 | " | 0 | " | " | " | " |
| 3 | " | 0 | " | 0 | " | " | " | " |
| 4 | " | 0 | " | 0 | " | " | " | " |
| 5 | " | 0 | " | " | " | " | " | " |
| 6 | " | 0 | " | " | " | " | " | " |
| TOTAL | 0 | 1 | 0 | 0 | 0 | 0 | 0 | 0 |

GENERAL TOTAL: 1
INDEX OF PRIMARY IRRITATION: 1/24 = 0.04

EXAMPLE 2

Filtrate of artichoke ("GYFAR")

Operation is carried out as described hereinabove for the algae, particularly as described in Example 1. A limpid brown filtrate is obtained.

Table V hereinbelow shows the results of analysis of the filtrate of artichokes.

EXAMPLE 3

Filtrate of algae (Ascophylum)

Operation is carried out as in Example 1 hereinabove, but using an alga Ascophylum.

Table VI herebelow shows the results of analysis of this filtrate "GYFA" and Table VII hereinbelow shows the results of analysis of the ash of this filtrate.

The invention may be applied to all plants containing useful elements; mention will also be made for example of the Calendula, horsetail, etc . . .

STUDY OF THE ASSIMILATION OF CERTAIN ELEMENTS AS A FUNCTION OF THE PRESENCE AND QUANTITY OF FILTRATE OF ALGAE GYFL INGESTED

Modus operandi
10 ♂ WISTAR rats used in experimentation
4 ♂ WISTAR rats used as controls.

Food used: feed U.A.R. REF. A.04
The body weight of the animals is indicated in Table VIII hereinbelow.

TABLE V

| RESULTS OF THE ANALYSIS | |
|---|---|
| | GYFAR (artichokes) |
| SODIUM (Na) mg/kg | 1950 |
| POTASSIUM (K) mg/kg | 4200 |
| LITHIUM (Li) µg/kg | 120 |
| CALCIUM (Ca) mg/kg | 1700 |
| MAGNESIUM (Mg) mg/kg | 118 |
| STRONTIUM (Sr) mg/kg | 11.6 |
| CHROMIUM (CR) mg/kg | <0.1 |
| IRON (Fe) mg/kg | 0.85 |
| MANGANESE (Mn) mg/kg | 4.75 |
| COPPER (Cu) mg/kg | 2.6 |
| COBALT (Co) µg/kg | <50 |
| NICKEL (Ni) µg/kg | <50 |
| MOLYBDENUM (Mo) µg/kg | <20 |
| ZINC (Zn) µg/kg | 0.38 |
| TIN (Sn) mg/kg | 57 |
| LEAD (Pb) mg/kg | <0.1 |
| CADIUM (Cd) mg/kg | 0.042 |
| ANTIMONY (Sb) mg/kg | ≦0.01 |
| CHLORINE mg/kg | 5820 |
| PHOSPHORUS mg/kg | 353 |
| NITROGEN mg/kg | 611 |
| ARSENIC mg/kg | 0.07 |
| BORON mg/kg | 0.6 |
| IODINE mg/kg | 104 |
| BROMINE mg/kg | 40 |
| SULFUR mg/kg | 301 |

LIPIDES 0.19%
PROTIDES 0.38%
GLUCIDES 0.31%
LD 50: >25 g/kg

TABLE VI

| RESULTS OF ANALYSES GYFA | | | |
|---|---|---|---|
| ORGANIC SUBSTANCES | | | |
| PROTEINS | | 0.030% | |
| LIPIDES | | 0.005% | |
| GLUCIDES | | 0.032% | |
| MINERALS | | | |
| SODIUM (Na) mg/kg | 290 | LEAD (Pb) mg/kg | <0.1 |
| POTASSIUM (K) mg/kg | 370 | CADMIUM (Cd) mg/kg | 0.124 |
| LITHIUM (Li) µg/kg | ≦2.5 | ANTIMONY (Sb) mg/kg | ≦0.01 |
| CALCIUM (Ca) µg/kg | 42 | CHLORINE (Cl) mg/kg | 387 |
| MAGNESIUM (Mg) µg/kg | 53 | PHOSPHORUS (P) mg/kg | 145 |
| STRONTIUM (Sr) µg/kg | 0.25 | NITROGEN (N) mg/kg | 49 |
| CHROMIUM (Cr) µg/kg | <0.1 | ARSENIC (As) mg/kg | 0.77 |
| IRON (Fe) µg/kg | 8 | BORON (B) mg/kg | 1.53 |
| MANGANESE (Mn) µg/kg | 0.35 | IODINE (I) mg/kg | 23 |
| COPPER (Cu) µg/kg | 1.85 | BROMINE (B2) mg/kg | <1 |
| COBALT (Co) µg/kg | <50 | SULFUR (S) mg/kg | 31 |
| NICKEL (Ni) µg/kg | 110 | TITANIUM (Ti) mg/kg | <1 |
| MOLYBDENUM (Mo) µg/kg | <20 | FLUORINE (F) mg/kg | 8.2 |
| ZINC (Zn) µg/kg | 0.57 | MERCURY (Hg) mg/kg | <0.05 |
| TIN (Sn) mg/kg | 15 | SELENIUM (Se) mg/kg | |
| AMINO ACIDS (in % on the M.S.) | | | |
| ALANINE | 0.209 | ARGININE | 0.128 |
| GLYCINE | 0.175 | LYSINE | 0.172 |
| VALINE | 0.189 | CYSTEINE | 0.078 |
| LEUCINE | 0.243 | METHIONINE | 0.018 |
| ISOLEUCINE | 0.133 | TYROSINE | 0.060 |
| GLUTAMIC ACID | 0.534 | PHENYLALANINE | 0.154 |
| ASPATRIC ACID | 0.476 | HISTIDINE | 0.075 |
| THEONINE | 0.156 | PROLINE | 0.135 |
| SERINE | 0.146 | TRYPTOPHANE | 0.022 |

TABLE VII

| RESULTS OF ANALYSIS | | | | |
|---|---|---|---|---|
| The results are expressed in percentage of wet product | | | | |
| | | ORGANIC SUBSTANCES | | |
| SAMPLES | ASH | Proteins | Lipides | Glucides* |
| GYFA | 0.138% | 0.030% | 0.005% | 0.032% |

*expressed in "glucose equivalent"

TABLE VIII

| RATS | Body weight |
|---|---|
| $N_1$ | 126 g |
| $N_2$ | 118 g |
| $V_1$ | 120 g |
| $V_2$ | 127 g |
| $R_1$ | 130 g |
| $R_2$ | 115 g |
| $Bl_1$ | 110 g |
| $Bl_2$ | 105 g |
| $B_1$ | 120 g |
| $B_2$ | 120 g |
| $T_1$ | 135 g |
| $T_2$ | 130 g |
| $T_3$ | 118 g |
| $T_4$ | 121 g |

From 23rd September and up to 5th October, $N_1$ and $N_2$ received by gastric cramming 0.5 ml of filtrate GYFL per day. On 4th and 5th October, the drinking water of rats $N_1$, $N_2$, $V_1$, $V_2$, $R_1$, $R_2$, $BL_1$, $BL_2$, $B_1$, $B_2$ was replaced by a 10% aqueous solution of filtrate GYFL.

No abnormality was observed in the behaviour of rats $N_1$ and $N_2$.

The 10% solution of filtrate was not repeated as drink; the quantity drunk was quite comparable with that usually ingested.

STUDY OF THE ASSIMILATION OF THE GLUCOSE

After ingestion, at time T, by gastric cramming of 0.5 ml of a glucose solution in different excipients, the development of glycaemia of the rats is followed every 15 minutes.

| Solution No. 1 | Glucose | 50 g |
| | Water qsp | 1000 ml |
| Solution No. 2 | Glucose | 50 g |
| | Filtrate GYFL | 100 ml |
| | Water qsp | 1000 ml |
| Solution No. 3 | Filtrate GYFL | 100 ml/l |
| | Glycerine | 10 ml/L |
| | Glucose | 200 g/L |
| | Fructose | 75 g/L |
| | Bl | 20 mg/L |
| | C | 5 g/L |
| | Sodium | 3 g/L |
| | Citric acid | pH 3.2 qsp |
| | Lemon flavour | 1.5 g/L |
| | Aerated water | 1000 ml qsp |

Rats
$N_1$ and $N_2$ received solution No. 1
$R_1$ and $R_2$ received solution No. 1
$B_1$ and $B_2$ received solution No. 2
$T_1$ and $T_2$ received solution No. 1
$BL_1$ and $BL_2$ received solution No. 3

Figure 3:
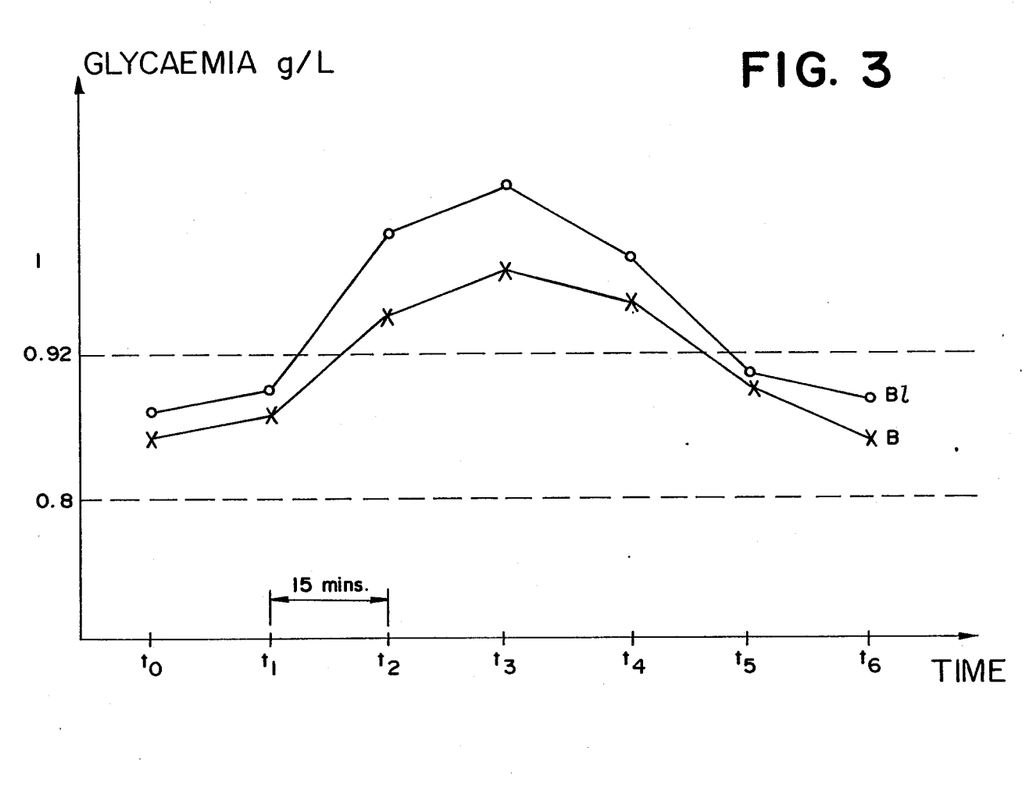

The results are shown in Table IX hereinbelow and in accompanying FIG. 3.

CONCLUSIONS

1. A clear hypoglycaemic shock is observed in the rats not subjected beforehand to a diet of algae and having ingested an aqueous solution of glucose exempt of algae.

2. A very slight hypoglycaemic shock is observed in the rats subjected beforehand to a small diet of algae and having ingested an aqueous solution of glucose.

3. No hypoglycaemic shock is observed in the rats subjected beforehand to a large or inexistent diet of algae, having ingested an aqueous solution of glucose with 10% of filtrate GYFL. There appears to be a better assimilation and use of the glucose ingested.

4. There appears to be storage of the glucose ingested in the case of the rats subjected beforehand to a considerable, long-duration diet of algae. In fact, there is neither hyper- nor hypoglycaemia.

Figure 4:
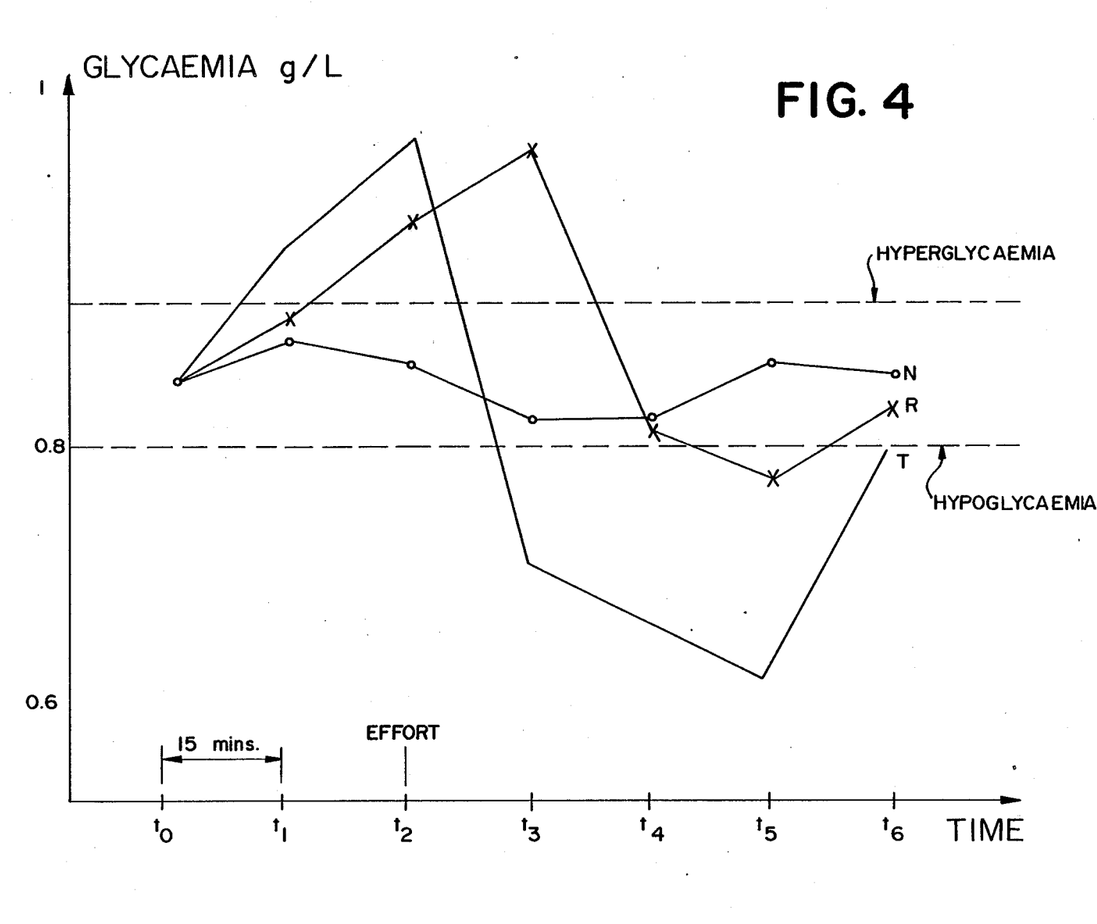

To support this hypothesis, a considerable effort was imposed at time $T_2$ on rats $R_2$ and $N_1$: the hypoglycaemia of $R_2$ is high, that of $N_1$ is zero, as may be seen in accompanying FIG. 4.

EXAMPLE 4

A filtrate of algae *Laminaria saccharrina* or *Ulva lactica* is prepared as indicated hereinabove.

It has been observed that, is the final extract thus obtained, or "physiological filtrate", is incorporated in drinks, the energy value of the drink is surprisingly increased. This increase has no connection with the nutritive value of the algae, and is therefore due to a synergistic effect.

The "cream of algae" and "protoexoplasma of algae" cannot be used for making drinks.

On the other hand, the "physiological filtrate" defined hereinabove may be added to any non-alcoholic drink, generally at a dose of 2 to 10%, particularly to fruit juices.

In fact, this filtrate may virtually constitute a drink by itself. A drink constituted by 99% of "physiological filtrate" and 1% of natural flavourings and additives may thus be created.

Table X hereinbelow gives a preferred list of algae which may be used in food.

TABLE IX

| | | | RESULTS OF GLYCAEMIA | | | | | | |
|---|---|---|---|---|---|---|---|---|---|
| | | $T_0$ | $T_1$ | $T_2$ | $T_3$ | $T_4$ | $T_5$ | $T_6$ | $T_n = T_{n-1} + 15'$ |
| Glucose + water | $R_1$ | 0.86 | 0.90 | 0.98 | 1.05 | 0.80 | 0.75 | 0.83 | rats subjected to a small diet of algae |
| | $R_2$ | 0.87 | 0.92 | 0.99 | 1.03 | 0.83 | 0.78 | 0.84 | of short duration |
| Glucose + water + filtrat | $B_1$ | 0.88 | 0.89 | 0.93 | 0.99 | 0.95 | 0.89 | 0.86 | rats subjected to a small diet of |
| | $B_2$ | 0.83 | 0.83 | 0.96 | 0.98 | 0.99 | 0.92 | 0.83 | algae of short duration |
| Drink | $BL_1$ | 0.86 | 0.86 | 1.03 | 1.05 | 1.01 | 0.90 | 0.87 | rats subjected to a small diet of |
| | $BL_2$ | 0.87 | 0.90 | 1.01 | 1.06 | 1.00 | 0.89 | 0.88 | algae of short duration |
| Glucose + water | $T_1$ | 0.85 | 0.98 | 1.05 | 0.70 | 0.65 | 0.60 | 0.79 | rats not subjected to a diet |
| | $T_2$ | 0.85 | 0.96 | 1.07 | — | 0.65 | 0.66 | 0.81 | of algae |
| Glucose + water | $N_1$ | 0.87 | 0.89 | 0.87 | — | 0.80 | 0.89 | 0.85 | rats subjected to a diet of algae for |
| | $N_2$ | 0.88 | 0.88 | 0.86 | 0.82 | 0.87 | 0.86 | 0.89 | 12 days beforehand (large and of long duration) |

TABLE X

List of the algae which may be used in food

| Genus | Ulva | Enteromorpha |
|---|---|---|
| | Laminaria | Cladophora |

TABLE X-continued

List of the algae which may be used in food

| | |
|---|---|
| Rhodymenia | Chodium |
| Chondrus | Lomentaria |
| Fucus | Gastrocelonium |
| Spirulina | Ceramium |
| Bracchiomonas | Ectocarpus |
| Platymonia | Paonia |
| Ulothrix | Coradophylum |
| Alaria | Pelvetia |
| Himanthalia | Bifurcaria |
| Cystosera | Gelidium |
| Dilcea | Furcellaria |
| Cystoclonium | Gigartina |
| Callibepharis | Gracilaria |
| Paliara | Laurencia |

EXAMPLE 5

A less preferred variant of the invention will be described hereinbelow, which does not comprise the final step of ultra-filtration.

The algae *Laminaria saccharina* or *Ulva lactuca* are used.

A protoexoplasma of algae is prepared as described hereinabove (cf. FIG. 2).

It is observed that, if the final extract thus obtained is incorporated in food, the energy value of the food is surprizingly increased. This increase is without connection with the nutritive value of the algae, and is therefore due to a synergistic effect.

This property was demonstrated by the following test.

A group of rats of WISTAR strain (control batch) was subjected to a diet composed of standard feed UAR reference A.04 (composition in Table XI hereinbelow), and two other batches of rats of the same strain were subjected to a diet based on the same feed supplemented by a "cream of algae" of *Laminaria saccharina* (P2) for one and by a "protoexoplasma" (P1) of the same variety of algae for the other.

The following appeared from the 10th day of treatment:

a significant reduction in weight of the feed absorbed per day and per rat, a substantially equivalent weight curve of the rats treated with respect to that of the controls.

Figure 5:
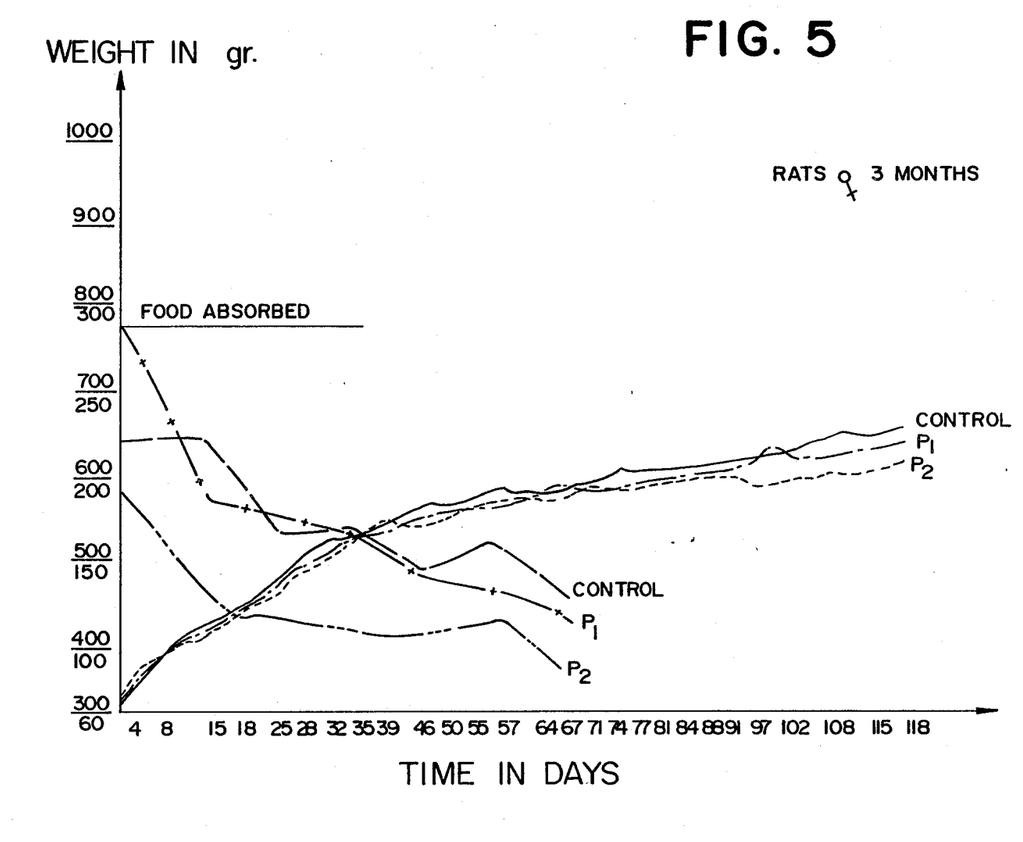
Figure 6:
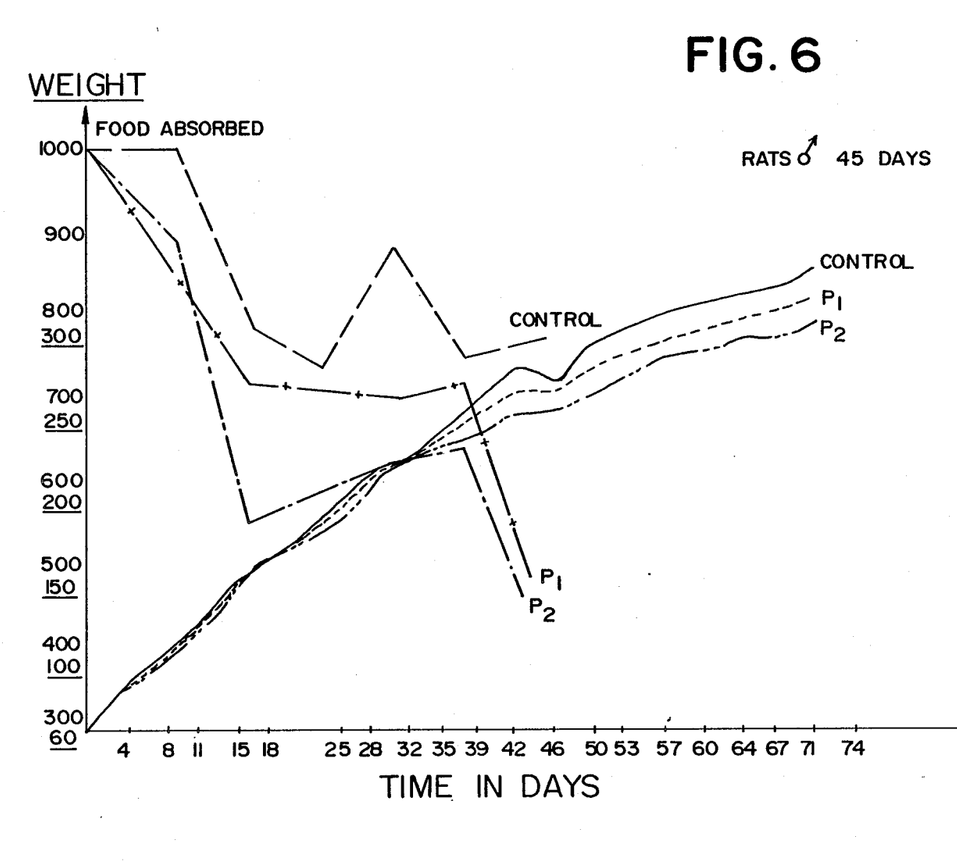

FIGS. 5 and 6 of the accompanying drawings show these curves. Moreover, although the reduction in weight of feed absorbed is obvious, no other phenomena showing any aggravation of the general state of the rats treated appeared (drop in weight, state of prostration, state of stress, ... ).

A nutritional character of the tested algae products may thus be deduced, which is difficult to understand if the potentializer character of this type of product is not admitted. In fact, if the composition of feed U.A.R. A.0.4 (Table XI hereinbelow) is compared with that of the algae products P1 and P2 (Table XII and XIII hereinbelow), it will be observed that, at equal weight, the algae products have a clearly higher nutritional value, for example on the 30th day of treatment, 1 g of P1 corresponds to 24.14 g-20 g=4.86 g of UAR feed without their composition expressed in percentages being comparable.

To support this hypothesis, on the 67th day of treatment, an assessment was made, on female rats, of the urinary excretion of 1-methylhistidine of the rats treated with respect to the control rats by C.C.M. on silica plate and revelation by ninhydrin, the intensity of the colour blue observed being a function of the quantity of amide acid having migrated. The assessment of methylhistidine excreted by the rats treated with respect to the control rats was made by sight.

No significant increase in the urinary excretion of 1-methylhitidine was observed.

The algae in question are absolutely non-toxic.

The "creams of algae" or the "protoexoplasma of algae" may therefore be used in the following foods, particularly:

| Food | Cream of algae | Protoexoplasma of algae | % by weight of algae product with respect to the weight of the food |
|---|---|---|---|
| Bread | X | X | 0 to 20 |
| Bread products | X | X | 0 to 10 |
| Enrichment of sauces | X | X | 0 to 80 |
| Patés, conserves, cooked meat or fish dishes | X | X | 0 to 20 |
| Pasta, wheaten and buckwheat pancakes | X | X | 0 to 25 |
| Confectionery | X | X | 0 to 20 |

The following non-limiting tests were made:

EXAMPLE A

Pancakes were made in accordance with a traditional recipe, incorporating 5, 10 or 15% of cream of algae *Laminaria saccharina*.

EXAMPLE B

Boiled sugar sweets were made, incorporating in a traditional recipe 1, 2, 3, 5 or 10% of cream of algae *Laminaria saccharina*.

EXAMPLE C

A meat paté was prepared, with 1 or 2% of cream of algae *Laminaria saccharina*, value in dry matter.

EXAMPLE D

A fruit cake was prepared, containing 1 or 2% of cream of algae *Laminaria saccharina*, value in dry matter.

EXAMPLE E

A sandwich loaf was prepared with 1 or 2% of cream of algae *Laminaria saccharina*, value in dry matter.

EXAMPLE F

A chewing gun manufactured, containing 2 or 5% of cream of algae laminaria saccharina.

EXAMPLE G

Bread was prepared from a traditional dough in which 5 or 10% cream of algae Laminaria saccharina was incorporated.

It was unnecessary to take any special precautions for any of these preparations. No unpleasant taste nor smell was noted.

TABLE XI

FEED U.A.R A.04

MINERALS (calculated in mg/kg)

|    | Natural Supply (average) | Supply by inorganic compound | TOTALS |
|----|-----|-----|-----|
| P  | 5 900 | 0 | 5 900 |
| Ca | 3 000 | 3 000 | 6 000 |
| K  | 6 000 | 0 | 6 000 |
| Na | 800 | 1 600 | 2 400 |
| Mg | 2 000 | 130 | 2 130 |
| Mn | 40 | 40 | 80 |
| Fe | 90 | 150 | 240 |
| Cu | 14 | 15 | 29 |
| Zn | 40 | 45 | 85 |
| Co | 0.05 | 1.50 | 1.55 |
| I  | supplied in assimilable form by marine algae | | |

VITAMINS (calculated to the kg)

|  | Natural supply (average) | Synthetic supply | TOTALS |
|--|-----|-----|-----|
| Vitamin A | 1 000 UI | 7 500 UI | 8 500 UI |
| Vitamin D 3 | 20 UI | 2 000 UI | 2 020 UI |
| Vitamin B 1 | 6 mg | 1 mg | 7 mg |
| Vitamin B 2 | 2 mg | 4.50 mg | 6.50 mg |
| Vitamin B 3 | 10 mg | 6.50 mg | 16.50 mg |
| Vitamin B 6 | 1.40 mg | 0.75 mg | 2.15 mg |
| Vitamin B 12 | 0.009 mg | 0.01 mg | 0.019 mg |
| Vitamin E | 18 mg | 15 mg | 33 mg |
| Vitamin K 3 | 0.25 mg | 2.25 mg | 2.50 mg |
| Vitamin PP | 60 mg | 15 mg | 75 mg |
| Folic acid | 0.50 mg | 0 mg | 0.50 mg |
| Biotin | 0.04 mg | 0 mg | 0.04 mg |
| Choline | 1 180 mg | 400 mg | 1 580 mg |

| FORMULA | % |
|---|---|
| Cereals, sugar | 83.1 |
| Vegetable proteins (cakes) | 6.9 |
| Animal proteins (fish) | 6 |
| Inorganic compound containing vitamins | 4 |

| MEAN ANALYSIS | % |
|---|---|
| Calorific value (Cal/kg) | 2900 |
| Water | 12 |
| Protides | 17 |
| Lipides | 3 |
| Glucides (E.N.A.) | 58.7 |
| Celluluose (Weende) | 4.3 |
| Minerals | 5 |

| AMINE ACIDS (calculated in mg/kg) | |
|---|---|
| Arginine | 9800 |
| Cystine | 2300 |
| Lysine | 8500 |
| Methionine | 3200 |
| Tryptophane | 1900 |
| Glycine | 8100 |

Daily ration of the rat: depending on the age and the weight from 18 to 25 g. water as desired
Daily ration of the mouse: depending on the age and the weight from 8 to 12 g. Water as desired.

TABLE XII

CHEMICAL COMPOSITION IDENTIFIED IN THE PROTOEXOPLASMA OF PHEOPHYCEA ALGAE ($P_1$)

| SUBSTANCES | in g per 100 g of dry matter | in mg/100 ml |
|---|---|---|
| Total ashes ($H_2SO_4$) | 27.0 | |
| Mineral nitrogen | 0.63 | 37.9 |
| Phosphorus | 0.10 | 6.0 |
| Iodine (iodate, iodide) | 0.16 | 9.4 |
| Chlorine | 6.84 | 410.7 |
| Sodium | 5.23 | 314.0 |
| Potassium | 6.47 | 388.0 |
| Calcium | 0.85 | 51.0 |
| Magnesium | 1.34 | 80.3 |
| Iron | 0.19 | 11.7 |
| Copper | 0.004 | 0.23 |
| Zinc | 0.015 | 0.92 |
| Manganese | 0.005 | 0.31 |
| Cobalt | — | <0.007 |
| *Energetic matter* | | |
| Amino nitrogen | 0.49 | |
| Total lipides | 0.70 | |
| *Identified sugars:* | | |
| Mannitol | 6.1 | |
| Fucose | 3.7 | |
| Glucose | none | |
| *Vitamins* | | |
| *Water-soluble vitamins* | | |
| B1 (Thiamine) | | none |
| B2 (Riboflavine) | | 0.34 |
| C (ascorbic acid) | | none |
| *Fat-soluble vitamins:* | | |
| A (Retinol) | | 1.5 |
| Provit.A (βcarotene) | | 0.60 |
| D (Calciferol) | | traces |
| E (Tocopherol) | | 4.86 |
| K (Phylloquinone) | | 0.056 |

TABLE XIII

|  | Cream of algae (P2) (% in dry substances) |
|---|---|
| Dry substances | 12 and 15 |
| Mineral nitrogen | 1.15 |
| Phosphorus | 0.10 |
| Iodine (iodate, iodide) | 0.10 |
| Chlorides | 3.54 |
| Sodium | 3.36 |
| Potassium | 4.60 |
| Calcium | 1.26 |
| Magnesium | 0.78 |
| Iron | 0.23 |
| Copper | 0.0015 |
| Zinc | 0.008 |
| Manganese | 0.004 |
| ENERGETIC SUBSTANCES | |
| Amino nitrogen | 0.31 |
| Total lipides | 0.16 |
| *Identified sugars* | |
| Mannitol | 1.48 |
| Fucose | 0.90 |
| VITAMINS | |
| *Water-soluble* | |
| B1 (thiamine) | 0.07 mg/100 g MS |
| B2 (riboflavine) | 0.65 mg/100 g MS |
| *fat-soluble* | |
| A (retinol) | 0.39 mg/100 g MS |
| Provit. A (βcarotene) | 13.47 mg/100 mg MS |
| D (Calciferol) | traces |
| E (tocopherol) | 1.17 mg/100 g MS |
| E (phylloquinone) | 0.013 mg/100 g MS |
| PHYTOHORMONES | |
| Gibberellines (GA1, GA3, GA4, GA7, GA9) | 50 μg/100 g MS |
| Auxines (iib, ANA, AIN, AIA) | |
| Cytokinines - Abscissines | |
| AMINO ACIDS | |
| Alanine | 0.209 |

TABLE XIII-continued

| | |
|---|---|
| Glycine | 0.175 |
| Valine | 0.189 |
| Leucine | 0.243 |
| Isoleucine | 0.133 |
| Glutamic acid | 0.534 |
| Aspartic acid | 0.476 |
| Threonine | 0.156 |
| Serine | 0.146 |
| Arginine | 0.128 |
| Lysine | 0.172 |
| Cysteine | 0.078 |
| Methionine | 0.018 |
| Tyrosine | 0.060 |
| Phenylalanine | 0.154 |
| Histidine | 0.075 |
| Proline | 0.135 |
| Tryptophane | 0.022 |

We claim:

1. A substantially sterile liquid physiological product obtained from a natural raw material selected from the group consisting of whole algae, whole plant, and parts thereof by cryocomminuting one of said algae and said plants to produce a pulp having a particle size of between about 100 to 10 microns; subjecting the pulp to molecular milling in a reciprocating piston-valve molecular-mill defining a space between said piston and said valve which causes bursting of vegetative cells and a release of large quantities of intracellular liquid; ultradecanting the molecular milled pulp to obtain a liquid protoexoplasma and a paste and then ultra-filtering said protoexoplasma on a filter having a membrane with a power of cut off of less than 20,000 in a sterile atmosphere thereby obtaining said substantially sterile, liquid physiological product.

2. The substantially sterile liquid physiological product of claim 1, wherein said natural raw material is algae.

3. A composition selected from the group consisting of a cosmetic composition, a drinkable composition, a food composition, a homeopathic composition, and a phytotherapeutic composition, comprising a substantially sterile liquid physiological product as defined in claim 2.

4. The substantially sterile liquid physiological product of claim 1, wherein said natural raw material is a plant.

5. A composition selected from the group consisting of a cosmetic composition, a drinkable composition, a food composition, a homeopathic composition, and a phytotherapeutic composition, comprising a substantially sterile liquid physiological product as defined in claim 4.

6. The substantially sterile liquid physiological product of claim 1, wherein said natural raw material is selected from the group consisting of the algae *Laminaria saccharina*, the algae *Ulva Lactina*, the Pheophycea algae, the Algae Ascophylum and the plant Artichoke.

7. A composition selected from the group consisting of a cosmetic composition, a drinkable composition, a food composition, a homeopathic composition, and a phytotherapeutic composition, comprising a substantially sterile liquid physiological product as defined in claim 6.

8. A composition selected from the group consisting of a cosmetic composition, a drinkable composition, a food composition, a homeopathic composition, and a phytotherapeutic composition, comprising a substantially sterile liquid physiological product as defined in claim 1.

9. A method of oligotherapy which comprises administering to a patient in need thereof an effective amount of the substantially sterile, liquid physiological product as defined in claim 1.

10. A method of oligotherapy which comprises administering to a patient in need thereof an effective amount of the substantially sterile, liquid physiological product as defined in claim 2.

11. A method of oligotherapy which comprises administering to a patient in need thereof an effective amount of the substantially sterile, liquid physiological product as defined in claim 6.

12. A method of oligotherapy which comprises administering to a patient in need thereof an effective amount of the substantially sterile, liquid physiological product as defined in claim 6.

13. The method of claim 9, wherein said substantially sterile, liquid physiological product is administered at a rate of from 10 to 50 ml per day.

14. The method of claim 10, wherein said substantially sterile, liquid physiological product is administered at a rate of from 10 to 50 ml per day.

15. The method of claim 11, wherein said substantially sterile, liquid physiological product is administered at a rate of from 10 to 50 ml per day.

16. The method of claim 12, wherein said substantially sterile, liquid physiological product is administered at a rate of from 10 to 50 ml per day.

17. A process of preparing a substantially sterile liquid physiological product from a natural raw product selected from the group consisting of whole algae, whole plants and parts thereof which comprises cryocommminuting one of said algae and said plants to produce a pulp having a particle size of between about 100 to 10 microns, subjecting the pulp to molecular milling in a reciprocating piston-valve molecular-mill defining a space between said piston and said valve which causes bursting of vegetative cells and a release of large quantities of intracellular liquid; ultra decanting the molecular milled pulp to obtain a liquid protoexoplasma and a paste and then ultra-filtering said protoexoplasma on a filter having a membrane with a power of cut off of less than 20,000 in a sterile atmosphere which results in the obtention of a substantially sterile, liquid physiological product.

18. The process of claim 17, wherein the space between piston and valve in the reciprocating piston-valve molecular mill is about 0.035 mm.

* * * * *